US012558186B2

(12) United States Patent
Shirazian et al.

(10) Patent No.: US 12,558,186 B2
(45) Date of Patent: Feb. 24, 2026

(54) SYSTEMS AND METHODS FOR TELESTRATION WITH SPATIAL MEMORY

(71) Applicant: Intuitive Surgical Operations, Inc., Sunnyvale, CA (US)

(72) Inventors: Pourya Shirazian, Menlo Park, CA (US); Mahdi Azizian, San Jose, CA (US); Daniel Proksch, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 529 days.

(21) Appl. No.: 17/781,315

(22) PCT Filed: Dec. 28, 2020

(86) PCT No.: PCT/US2020/067165
§ 371 (c)(1),
(2) Date: May 31, 2022

(87) PCT Pub. No.: WO2021/138262
PCT Pub. Date: Jul. 8, 2021

(65) Prior Publication Data
US 2022/0409324 A1      Dec. 29, 2022

Related U.S. Application Data

(60) Provisional application No. 62/954,823, filed on Dec. 30, 2019.

(51) Int. Cl.
*A61B 90/30* (2016.01)
*A61B 34/20* (2016.01)
*A61B 90/00* (2016.01)

(52) U.S. Cl.
CPC ...... *A61B 90/30* (2016.02); *A61B 2034/2059* (2016.02); *A61B 2090/363* (2016.02); *A61B 2090/372* (2016.02)

(58) Field of Classification Search
CPC ............ A61B 90/30; A61B 2034/2059; A61B 2090/363; A61B 2090/372; A61B 90/361;
(Continued)

(56) References Cited

U.S. PATENT DOCUMENTS 6,522,906 B1 * 2/2003 Salisbury, Jr. ....... A61B 1/0005
600/407
10,643,386 B2 * 5/2020 Li ........................... G06T 13/80
(Continued)

FOREIGN PATENT DOCUMENTS

| CN | 102318352 A | 1/2012 |
| CN | 103635909 A | 3/2014 |

(Continued)

OTHER PUBLICATIONS

Google Lens: The Coolest App You Aren't Using, uploaded on Jun. 18, 2019 by user "Digital Trends". Retrieved from Internet: https://www.youtube.com/watch?v=h_nYU9OVCZk>) (Year: 2019).*
(Continued)

*Primary Examiner* — Charles T Shedrick

(57) ABSTRACT

An exemplary system is configured to detect user input directing a telestration element to be drawn within an image depicting a surface within a scene; render, based on depth data representative of a depth map for the scene and within a three dimensional (3D) image depicting the surface within the scene, the telestration element; record a 3D position within the scene at which the telestration element is rendered within the 3D image; detect a telestration termination event that removes the telestration element from being rendered within the 3D image; and indicate, subsequent to the telestration termination event, an option to again render the telestration element at the 3D position.

20 Claims, 13 Drawing Sheets

(58) Field of Classification Search
CPC .............. A61B 34/30; A61B 2090/365; A61B
2090/371; G06V 20/20; G06V 30/32;
H04N 13/207; H04N 13/271; H04N
13/239; H04N 13/128; H04N 2013/0081
See application file for complete search history.

(56) References Cited

U.S. PATENT DOCUMENTS

| | | | | |
|---|---|---|---|---|
| 11,534,245 | B2 * | 12/2022 | Heaney | A61B 90/37 |
| 2007/0156017 | A1 * | 7/2007 | Lamprecht | A61B 1/00194 |
| | | | | 600/102 |
| 2007/0167702 | A1 * | 7/2007 | Hasser | A61B 90/36 |
| | | | | 600/407 |
| 2009/0036902 | A1 * | 2/2009 | DiMaio | A61B 8/12 |
| | | | | 606/130 |
| 2010/0164950 | A1 * | 7/2010 | Zhao | A61B 34/20 |
| | | | | 345/419 |
| 2010/0317965 | A1 * | 12/2010 | Itkowitz | A61B 34/30 |
| | | | | 382/128 |
| 2011/0118753 | A1 * | 5/2011 | Itkowitz | A61B 34/74 |
| | | | | 606/130 |
| 2011/0304691 | A1 | 12/2011 | Newton et al. | |
| 2012/0071891 | A1 * | 3/2012 | Itkowitz | G05B 15/02 |
| | | | | 715/863 |
| 2013/0165186 | A1 * | 6/2013 | Choi | H04N 13/128 |
| | | | | 455/566 |
| 2014/0111623 | A1 * | 4/2014 | Zhao | H04N 13/128 |
| | | | | 348/47 |
| 2014/0267549 | A1 | 9/2014 | Pinter et al. | |
| 2014/0344758 | A1 | 11/2014 | Kozakura | |
| 2016/0092732 | A1 * | 3/2016 | Black | G06T 19/006 |
| | | | | 382/103 |
| 2016/0371885 | A1 | 12/2016 | Gavriliuc et al. | |
| 2018/0042680 | A1 * | 2/2018 | DiMaio | G16H 20/40 |
| 2019/0182454 | A1 * | 6/2019 | Berger | G16H 30/40 |
| 2021/0141498 | A1 | 5/2021 | Magureanu et al. | |
| 2021/0369370 | A1 * | 12/2021 | Malanowski | A61G 13/04 |
| 2024/0249498 | A1 * | 7/2024 | Galeotti | G06N 3/096 |

FOREIGN PATENT DOCUMENTS

| | | | | |
|---|---|---|---|---|
| CN | 104012079 A | 8/2014 | | |
| CN | 104582622 A | 4/2015 | | |
| CN | 105122309 A | 12/2015 | | |
| CN | 108095761 A | 6/2018 | | |
| EP | 2498711 B1 * | 1/2018 | | A61B 34/37 |
| WO | WO-02100284 A1 * | 12/2002 | | G02B 27/017 |
| WO | WO-2007120351 A2 | 10/2007 | | |

OTHER PUBLICATIONS

International Preliminary Report on Patentability for Application No. PCT/US2020/067165, mailed on Jul. 14, 2022, 08 pages.
International Search Report and Written Opinion for Application No. PCT/US2020/067165, mailed Apr. 15, 2021, 11 pages.
Penne J., et al., "Time-of-Flight 3-D Endoscopy," Big Data Analytics in the Social and Ubiquitous Context: 5th International Workshop on Modeling Social Media, MSM 2014, 5th International Workshop on Mining Ubiquitous and Social Environments, MUSE 2014 and First International Workshop on Machine, Sep. 20, 2009, vol. 12 (1), pp. 467-474.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Office Action for Chinese Application No. CN202080088189, mailed Jan. 26, 2025, 31 pages.

\* cited by examiner

1100

SYSTEMS AND METHODS FOR TELESTRATION WITH SPATIAL MEMORY

RELATED APPLICATIONS

The present application is a U.S. National Stage Application under 35 U.S.C. § 371 of International Application No. PCT/US2020/067165, filed on Dec. 28, 2020, which claims priority to U.S. Provisional Patent Application No. 62/954,823, filed Dec. 30, 2019, the contents of which are hereby incorporated by reference in their entirety.

BACKGROUND INFORMATION

A computer-assisted surgical system often includes a user control system configured to facilitate remote control by a surgeon of one or more surgical instruments used to perform a surgical procedure. In some configurations, the user control system includes a stereo viewer having two display devices configured to present a three-dimensional ("3D") image of a surgical scene to the surgeon during the surgical procedure. The 3D image provides the surgeon with depth perception during the surgical procedure. A two-dimensional ("2D") image of the surgical scene may be concurrently presented to other surgical team members (e.g., a medical assistant) by way of a separate display device. In this manner, the surgical team members can visualize the procedure being performed and assist as necessary.

For example, in some instances, a surgical team member may desire to bring something (e.g., tissue or an object) in the scene to the attention of the surgeon. To this end, the surgical team member may draw an object on the 2D image (e.g., a circle around a depiction of tissue of interest). Using telestration technology, the drawn object may be displayed on one of the display devices included in the stereo viewer so that the surgeon can see what was drawn.

Unfortunately, because the drawn object (also referred to herein as a telestration element) is in 2D, the drawn object may appear to be "floating" or otherwise not really integrated into the 3D image viewed by the surgeon. Moreover, when there are multiple telestration elements (e.g., multiple drawn objects) drawn by surgical team member(s) during a surgical session, it may be difficult for the surgeon to remember all of the information that the telestration elements were intended to convey.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary system includes a memory storing instructions and a processor communicatively coupled to the memory and configured to execute the instructions to detect user input directing a telestration element to be drawn within an image depicting a surface within a scene; render, based on depth data representative of a depth map for the scene and within a 3D image depicting the surface within the scene, the telestration element (e.g., to visually appear as being in physical contact with the surface); record a 3D position within the scene at which the telestration element is rendered within the 3D image; detect a telestration termination event that removes the telestration element from being rendered within the 3D image; and indicate, subsequent to the telestration termination event, an option to again render the telestration element at the 3D position.

Another exemplary system includes a memory storing instructions and a processor communicatively coupled to the memory and configured to execute the instructions to detect user input directing a telestration element to be drawn within a first image depicting a scene; render, in response to the user input, the telestration element within a second image depicting the scene; record a position within the scene at which the telestration element is rendered within the second image; detect a telestration termination event that removes the telestration element from being rendered within the second image; and indicate, subsequent to the telestration termination event and within the second image, an option to again render the telestration element within the second image at the position.

An exemplary method includes detecting, by a telestration element management system, user input directing a telestration element to be drawn within an image depicting a surface within a scene; rendering, by the telestration element management system based on depth data representative of a depth map for the scene and within a 3D image depicting the surface within the scene, the telestration element; recording, by the telestration element management system, a 3D position within the scene at which the telestration element is rendered within the 3D image; detecting, by the telestration element management system, a telestration termination event that removes the telestration element from being rendered within the 3D image; and indicating, by the telestration element management system subsequent to the telestration termination event, an option to again render the telestration element at the 3D position.

An exemplary non-transitory computer-readable medium stores instructions that, when executed, direct a processor of a computing device to detect user input directing a telestration element to be drawn within an image depicting a surface within a scene; render, based on depth data representative of a depth map for the scene and within a 3D image depicting the surface within the scene, the telestration element; record a 3D position within the scene at which the telestration element is rendered within the 3D image; detect a telestration termination event that removes the telestration element from being rendered within the 3D image; and indicate, subsequent to the telestration termination event, an option to again render the telestration element at the 3D position.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
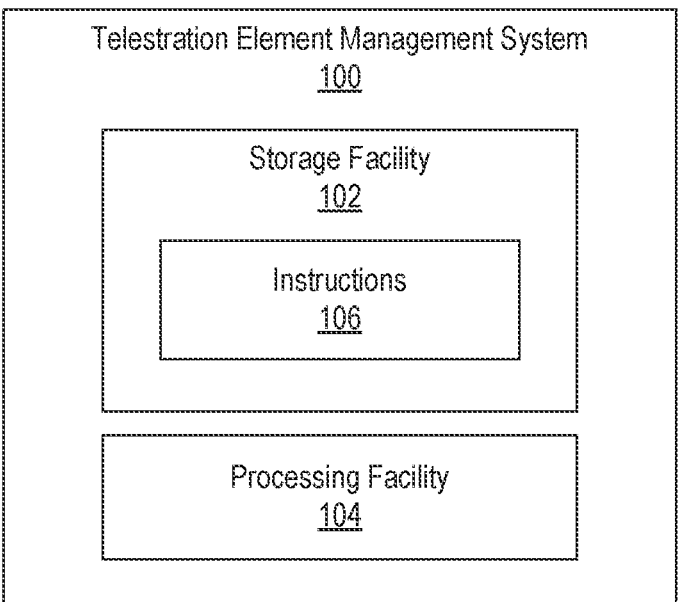
FIG. 1 illustrates an exemplary telestration element management system according to principles described herein.

Telestration element management systems and methods are described herein. As described herein, an exemplary telestration element management system may detect user input directing a telestration element to be drawn within an image (e.g., on a 2D image or a 3D image) depicting a surface (e.g., a tissue surface) within a scene (e.g., a surgical area associated with a patient). Based on depth data representative of a depth map for the scene and within a 3D image depicting the surface within the scene, the telestration element management system may render the telestration element (e.g., to visually appear as being in physical contact with the surface). The telestration element management system may record a 3D position within the scene at which the telestration element is rendered within the 3D image, detect a telestration termination event that removes the telestration element from being rendered within the 3D image, and indicate (e.g., graphically and/or audibly), subsequent to the telestration termination event, an option to again render the telestration element at the 3D position.

As another example, an exemplary telestration element management system may detect user input directing a telestration element to be drawn within a first image (e.g., a 2D image or a 3D image) depicting a scene and render, in response to the user input, the telestration element within a second image (e.g., a 3D image) depicting the scene. The telestration element management system may record a position (e.g., a 3D position) within the scene at which the telestration element is rendered within the second image, detect a telestration termination event that removes the telestration element from being rendered within the second image, and indicate, subsequent to the telestration termination event and within the second image, an option to again render the telestration element within the second image at the position.

The systems and methods described herein advantageously render, based on drawings in two dimensions, telestration elements in three dimensions with spatial memory in order to facilitate communication between a surgeon and one or more other surgical team members, such as a mentor, medical assistant, nurse, etc. As described herein, a rendered 3D telestration element may account for peaks, valleys, contours, and/or other variations in depth of a surface (e.g., an anatomical surface) on which the 3D telestration element is rendered. Systems and methods described herein record a 3D position at which the telestration element is rendered to provide spatial information associated with the rendered telestration element that may be used to again render the telestration element after the rendered telestration element is removed from the 3D image.

The systems and methods described herein may also advantageously record a timestamp and/or other metadata indicating when and by whom the telestration element is rendered to provide temporal, user, and/or other types of information associated with the rendered telestration element. Such a timestamp and/or other metadata can be used to provide time and user information about the telestration element after the rendered telestration element is removed from the 3D image.

The systems and methods described herein may also advantageously provide for selecting an object and/or placing fiducial markers within a first image (e.g., a 2D or 3D image) and indicating the selection of the object and/or placement of fiducial markers within a second image (e.g., a 3D image). Spatial and/or temporal information associated with the object selection and/or fiducial markers may also be used to facilitate communication between surgical team members.

These and other advantages and benefits of the systems and methods described herein will be made apparent herein.

As used herein, a telestration element refers to any drawing or graphic item placed by a user within a first image (e.g., a 2D image or a 3D image) that is to be rendered within a corresponding second image (e.g., a 3D image) and/or used for object selection within the second image. For example, a telestration element, such as a shape, a word, a symbol, etc., may be drawn by a user on a monitor or other display device displaying a 2D image of a scene and rendered, using telestration technology, within a 3D image of the scene displayed within a stereo viewer of a user control system.

In other examples, a telestration element, such as a circle or other shape, may be drawn on a 2D image to select an object within the 2D image. A classification heuristic (e.g., segmentation, machine learning, etc.) may determine that the drawn telestration element is intended to select the object and graphically indicate the selection of the object within a corresponding 3D image.

FIG. 1 illustrates an exemplary telestration element management system 100 ("system 100") configured to perform various operations described herein. As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). For example, facilities 102 and/or 104 may be implemented by any component in a computer-assisted surgical system. As another example, facilities 102 and/or 104 may be implemented by a computing device separate from and communicatively coupled to a computer-assisted surgical system. In some examples, facilities 102 and 104 may be distributed between multiple devices and/or multiple locations as may serve a particular implementation.

Storage facility 102 may maintain (e.g., store) executable data used by processing facility 104 to perform one or more of the operations described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations described herein.

For example, processing facility 104 may be configured to: detect user input directing a telestration element to be drawn within an image depicting a surface within a scene; render, based on depth data representative of a depth map for the scene and within a 3D image depicting the surface within the scene, the telestration element; record a 3D position within the scene at which the telestration element is rendered within the 3D image; detect a telestration termination event that removes the telestration element from being rendered within the 3D image; and indicate, subsequent to the telestration termination event, an option to again render the telestration element at the 3D position.

As another example, processing facility 104 may be configured to: detect user input directing a telestration element to be drawn within a first image depicting a scene; render, in response to the user input, the telestration element within a second image depicting the scene; record a position within the scene at which the telestration element is rendered within the second image; detect a telestration termination event that removes the telestration element from being rendered within the second image; and indicate, subsequent to the telestration termination event and within the second image, an option to again render the telestration element within the second image at the position.

As another example, processing facility 104 may be configured to access image data representative of an image acquired by an imaging device and depicting an internal space of a patient, obtain depth data representative of a depth map for the internal space depicted in the image acquired by the imaging device, identify, based on the image data and the depth data, a 3D position within a 3D image that depicts a surface (e.g., an anatomical surface) onto which a telestration element is to be rendered, and instruct a display device to render the telestration element at the identified 3D position within the 3D image.

These and other operations that may be performed by system 100 (e.g., processing facility 104) are described herein.

Figure 2:
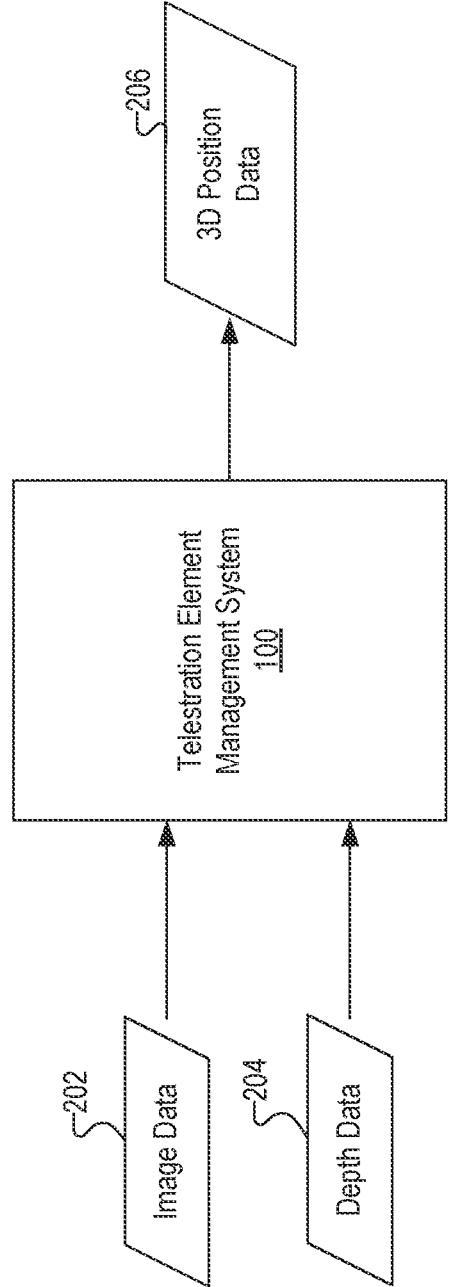
FIG. 2 illustrates an exemplary configuration in which a system is configured to identify a 3D position within an image acquired by an imaging device and that depicts a surface onto which a telestration element is to be rendered according to principles described herein.
Figure 2:

FIG. 2 illustrates an exemplary configuration 200 in which system 100 is configured to identify a 3D position within an image acquired by an imaging device and that depicts a surface onto which a telestration element is to be rendered. As shown, system 100 may access image data 202 representative of an image acquired by an imaging device and depicting an internal space of a patient. System 100 may also obtain depth data 204 representative of a depth map for the internal space depicted in the image acquired by the imaging device. Based on image data 202, depth data 204, and user input directing a telestration element to be drawn on a 2D image, system 100 may identify a 3D position within a 3D image that depicts a surface onto which the telestration element is to be rendered and output 3D position data 206 representative of the identified 3D position.

3D position data 206 may be in any suitable format. For example, 3D position data 206 may include 3D surface vertices representative of pixels that depict the surface onto which the telestration element is to be rendered within the 3D image. 3D position data 206 may also include 2D pixel coordinates representative of pixels detected as user input directing a telestration element to be drawn on a 2D image and that correlate or map to the 3D surface vertices.

Exemplary manners in which image data 202, depth data 204, and 3D position data 206 may be generated will now be described.

Figure 3:
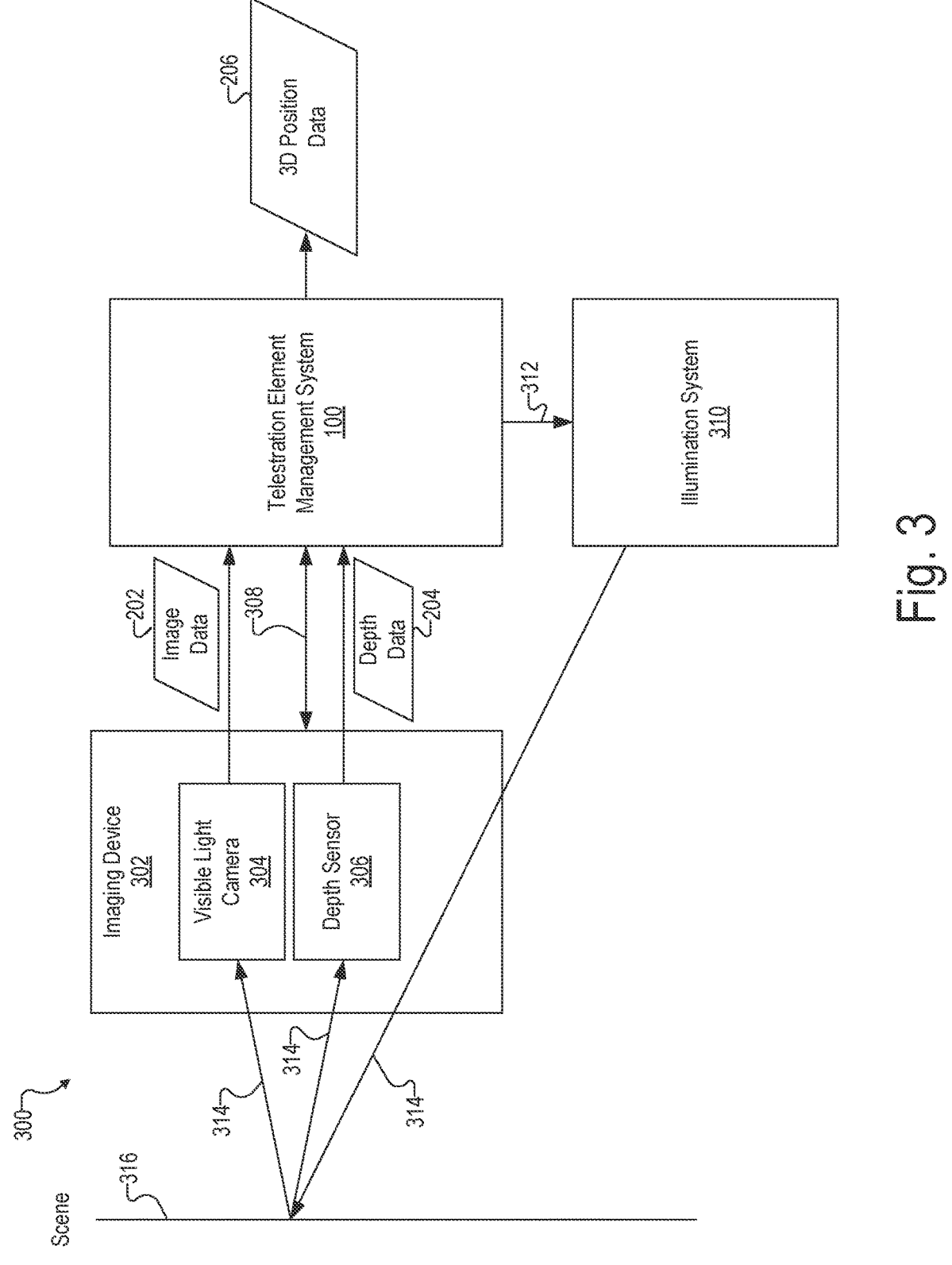
FIG. 3 illustrates an exemplary configuration in which an imaging device includes a visible light camera and a depth sensor according to principles described herein.

FIG. 3 illustrates an exemplary configuration 300 in which an imaging device 302 includes a visible light camera 304 configured to generate and output image data 202 and a depth sensor 306 configured to generate and output depth data 204.

Imaging device 302 may be implemented by an endoscope or other camera device configured to capture images of a scene. In some examples, imaging device 302 may be configured to be attached to and controlled by a computer-assisted surgical system. In alternative examples, imaging device 302 may be hand-held and operated manually by an operator (e.g., a surgeon).

In some examples, the scene captured by imaging device 302 may include a surgical area associated with a patient. The surgical area may, in certain examples, be entirely disposed within the patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments used to perform the surgical procedure are located. In certain example implementations, the surgical area entirely disposed within the patient may be referred to as an "internal space." As described herein, any internal anatomy of the patient (e.g., vessels, organs, and/or tissue) and/or surgical instruments located in the internal space may be referred to as objects and/or structures.

Visible light camera 304 ("camera 304") is configured to generate image data 202 representative of a two-dimensional visible light image of a scene. Camera 304 may be implemented by any suitable image sensor, such as a charge coupled device ("CCD") image sensor, a complementary metal-oxide semiconductor ("CMOS") image sensor, a hyperspectral camera, a multispectral camera, or the like.

Depth sensor 306 may be implemented by any suitable sensor configured to generate depth data 204. For example, depth sensor 306 may be implemented by a time-of-flight sensor, a structured light sensor, an interferometer, a hyperspectral camera, a multispectral camera, and/or any other suitable sensor configured to acquire depth data as may serve a particular implementation. In cases where depth sensor 306 is implemented by a time-of-flight sensor, the time-of-flight sensor may be implemented by one or more photodetectors (e.g., one or more single photon avalanche diode ("SPAD") detectors), CCD sensors, CMOS sensors, and/or any other suitable configuration. In the example of FIG. 3, depth sensor 306 is separate from (i.e., physically distinct from) camera 304.

In configuration 300, system 100 may obtain image data 202 by directing camera 304 to acquire image data 202 and receiving image data 202 from camera 304. Likewise, system 100 may obtain depth data 204 by directing depth sensor 306 to acquire depth data 204 and receiving depth data 204 from depth sensor 306.

To this end, in configuration 300, system 100 is communicatively coupled to imaging device 302 by way of a bidirectional communication link 308 and to an illumination system 310 by way of a communication link 312. Communication links 308 and 312 may each be implemented by any suitable wired and/or wireless communication medium as may serve a particular implementation. System 100 may use communication links 308 and 312 to direct camera 304 and depth sensor 306 to acquire image data 202 and depth data 204 and receive image data 202 and depth data 204, as described herein.

Illumination system 310 may be configured to emit light 314 (e.g., at the direction of system 100) used to illuminate a scene to be imaged by imaging device 302. The light 314 emitted by illumination system 310 may include visible light and/or non-visible light (e.g., infrared light). As shown, light 314 may travel to the scene through imaging device 302 (e.g., by way of an illumination channel within imaging device 302 that may be implemented by one or more optical fibers, light guides, lenses, etc.).

As shown, light 314 emitted by illumination system 310 may reflect off a surface 316 within a scene being imaged by imaging device 302. In cases where imaging device 302 is aimed at an internal space of the patient, surface 316 represents a surface (e.g., an anatomical surface) within the internal space.

Camera 304 and depth sensor 306 may each detect the reflected light 314. Camera 304 may be configured to generate, based on the detected light, image data 202 representative of a two-dimensional visible light image of the scene including surface 316. Depth sensor 306 may be configured to generate, based on the detected light, depth data 204. Image data 202 and depth data 204 may each have any suitable format.

To generate a stereoscopic image of a scene, system 100 may direct illumination system 310 to emit light 314. System 100 may also activate (e.g., turn on) visible light camera 304 and depth sensor 306. Light 314 travels to the scene and reflects off of surface 316 (and, in some examples, one or more other surfaces in the scene). Camera 304 and depth sensor 306 both detect the reflected light 314.

Camera 304 (and/or other circuitry included in imaging device 302) may generate, based on detected light 314, image data 202 representative of a two-dimensional visible light image of the scene. This may be performed in any suitable manner. Visible light camera 304 (and/or other circuitry included in imaging device 302) may transmit image data 202 to system 100. This may also be performed in any suitable manner.

Depth sensor 306 may generate, based on detected light 314, depth data 204 representative of a depth map of the scene (e.g., a depth map of surface 316). This may be performed in any suitable manner. For example, depth sensor 306 may measure an amount of time that it takes for a photon of light 314 to travel from illumination system 310 to depth sensor 306. Based on this amount of time, depth sensor 306 may determine a depth of surface 316 relative to a position of depth sensor 306. Data representative of this depth may be represented in depth data 204 in any suitable manner. For example, the depth map represented by depth data 204 may include an array of depth values (e.g., Z-buffer values) corresponding to each pixel in an image.

Depth sensor 306 (and/or other circuitry included in imaging device 302) may transmit depth data 204 to system 100. This may be performed in any suitable manner.

System 100 may receive image data 202 and depth data 204 and perform one or more processing operations on image data 202 and depth data 204. For example, as will be described in more detail below, system 100 may generate 3D position data 206 based on image data 202 and depth data 204.

As another example, system 100 may generate, based on image data 202 and depth data 204, a right-side perspective image representative of the scene and a left-side perspective image representative of the scene. This may be performed in any suitable manner. System 100 may then direct display devices to concurrently display the right and left-side perspective images in a manner that forms a stereoscopic image of the scene. In some examples, the display devices are included in and/or communicatively coupled to computer-assisted surgical system 204.

Figure 4:
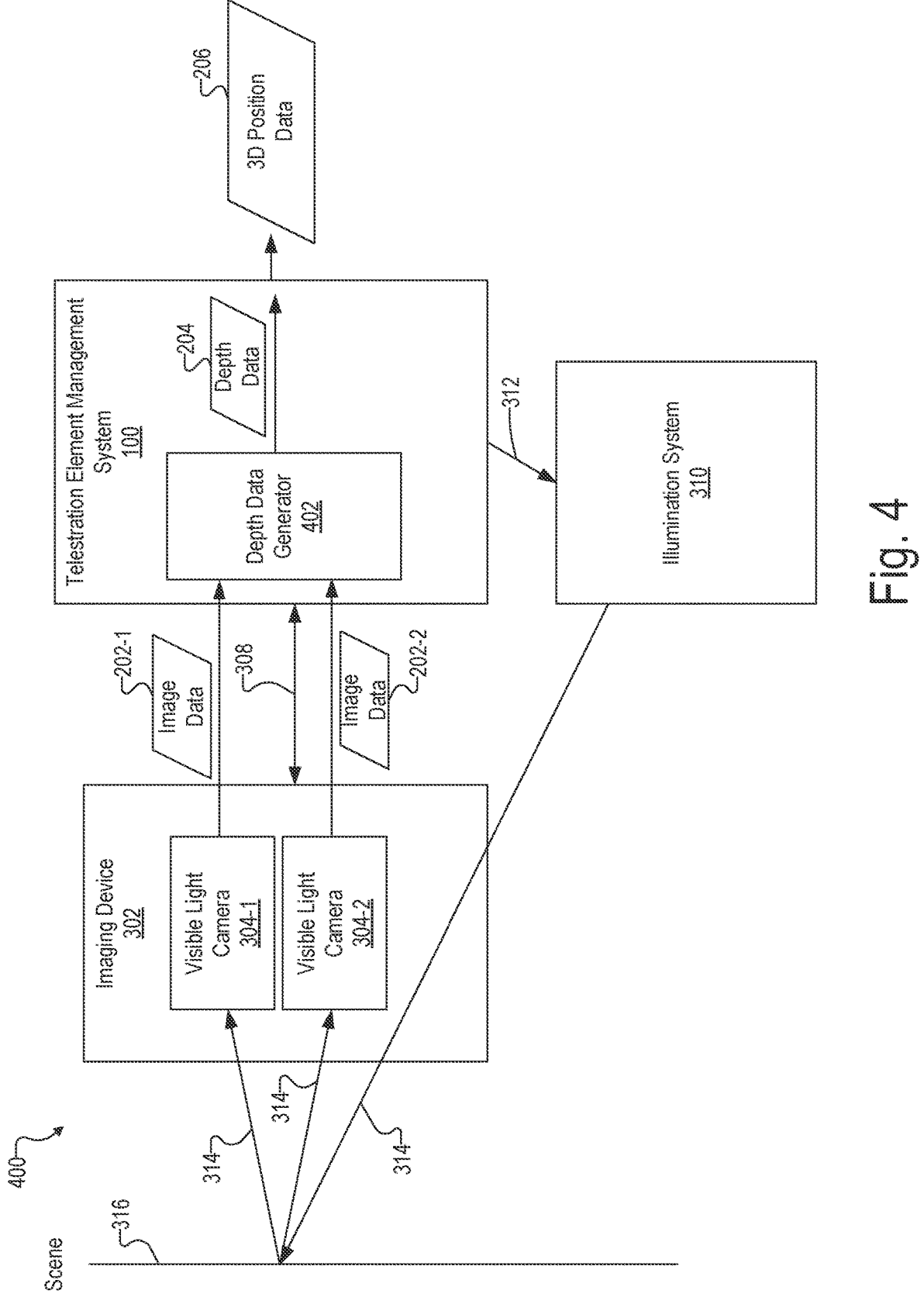
FIG. 4 illustrates an exemplary configuration in which a depth sensor is implemented by visible light cameras according to principles described herein.

FIG. 4 illustrates an exemplary configuration 400 in which depth sensor 306 is implemented by visible light cameras 304-1 and 304-2 included in imaging device 302. In configuration 400, system 100 may obtain depth data 204 by directing camera 304-1 to acquire a first image (e.g., a first two-dimensional image) of an internal space of a patient, directing camera 304-2 to acquire a second image (e.g., a second two-dimensional image) of the internal space of the patient, and generating, based on the first and second images, the depth map represented by depth data 204.

In FIG. 4, the first image acquired by camera 304-1 is represented by image data 202-1 and the second image acquired by camera 304-2 is represented by image data 202-2. As shown, image data 202-1 and 202-2 are transmitted to a depth data generator 402 implemented by system 100. Depth data generator 402 may use any visible image-based technique to determine depth data 204 based on image data 202-1 and 202-2.

Other configurations of imaging device 302 are possible in accordance with the systems and methods described herein. For example, imaging device 302 may include multiple cameras 304 and/or multiple depth sensors 306. To illustrate, imaging device 302 may include two cameras 304 in combination with a separate depth sensor 306. In these embodiments, depth data may be generated based on the images acquired by both cameras 304. Depth data generated by depth sensor 304 may be used to fine tune or otherwise enhance the depth data generated based on the images acquired by both cameras 304.

Figure 5:
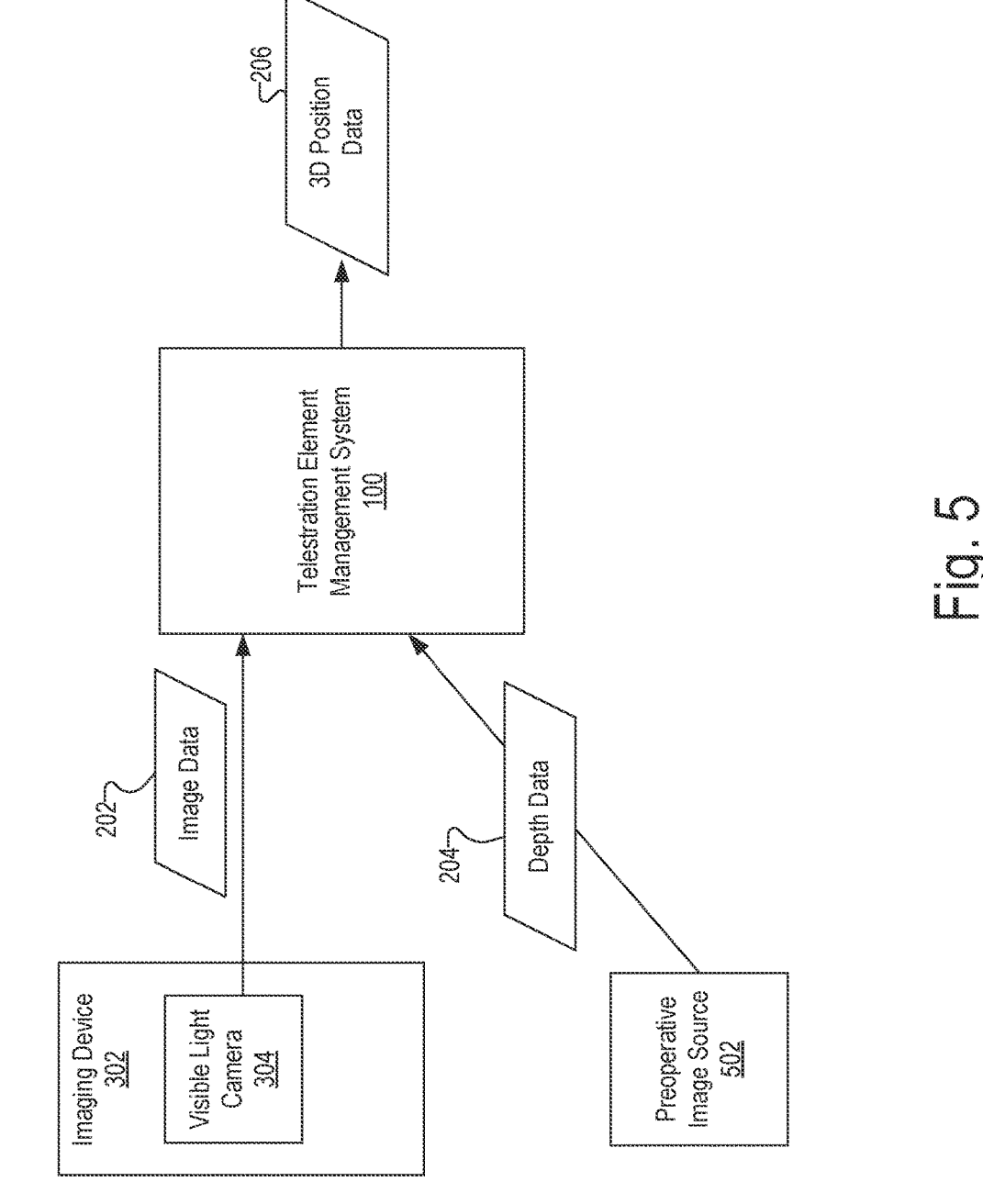
FIG. 5 shows an exemplary configuration in which a system obtains depth data from a preoperative image source according to principles described herein.

In some examples, system 100 may obtain depth data 204 by accessing a preoperative image registered to the image from a source other than imaging device 204. For example, FIG. 5 shows an exemplary configuration 500 in which system 100 obtains depth data 204 from a preoperative image source 502. Source 502 may be implemented by a computer-aided tomography (CT) scanner, a magnetic resonance imaging (MRI) device, an ultrasound device, a three-dimensional scanning (LIDAR) device, and/or any other suitable alternative imaging device configured to generate a preoperative image of the patient. The preoperative image may be registered with the image represented by image data 202 and thereby provide depth data 204.

3D position data 206 that indicates the 3D position at which a telestration element is rendered within a 3D image may be generated and output by system 100 based on image data 202, depth data 204, and user input directing the telestration element to be drawn on an image (e.g., a 2D image or a 3D image). This may be performed in any suitable manner. For example, system 100 may access image data 202 representative of the image acquired by the imaging device and obtain depth data 204 in any suitable way as described herein. System 100 may then identify, based on the image data, the depth data, and the user input, 3D position data 206 as a plurality of pixels within the 3D image that depict the 3D position at which the telestration element is to be rendered, and designate the plurality of pixels as the 3D position.

In other examples, system 100 may identify as user input, based on the drawn telestration element, a plurality of pixels on the 2D image represented by image data 202 that correlate to the drawn telestration element. System 100 may determine, based on depth data 204, depth values for each of the plurality of pixels that correlate to the telestration element to identify 3D position data 206 for rendering the telestration element within the 3D image. In other words, system 100 may identify 2D pixel coordinates representative of the telestration element drawn on the 2D image represented by image data 202 and then use depth data 204 to determine depth values for each of the 2D pixel coordinates to identify 3D position data 206 representative of pixels at which the telestration element is to be rendered within the correlating 3D image. Image data 202 and depth data 204 may be used to determine a location of a surface onto which the telestration element is to be rendered, a size of the surface, and/or any other characteristic of the surface. Accordingly, once rendered by system 100, the telestration element within the 3D image may visually appear as being in physical contact with a surface (e.g., an anatomical or organ surface) within the 3D image.

Once the 3D position for rendering a telestration element within a 3D image is obtained, system 100 may instruct a display system to render the telestration element at the identified 3D position within the 3D image. This may be performed in any suitable manner.

The rendered telestration element includes spatial memory as system 100 may record the 3D position represented by 3D position data 206 of the rendered telestration element. The recorded 3D position of the rendered telestration element may be used for subsequent recall and display after the telestration element has been removed from the 3D image.

Additionally or alternatively, systems and methods described herein may provide telestration elements with temporal memory and/or user memory. For example, in addition to recording a 3D position at which the telestration element is rendered within a 3D image to provide spatial information associated with the rendered telestration element, system 100 may record a timestamp of when the telestration element is rendered to provide temporal information associated with the rendered telestration element and/or metadata indicative of an identity of a user who provided the telestration element to provide user information associated with the rendered telestration element.

After rendering the telestration element, a telestration termination event may be detected. The telestration termination event is configured to remove the telestration element from being drawn on the first image (e.g., a 2D image) and/or from being rendered within the second image (e.g., a 3D image). Various telestration termination events may be detected, including but not limited to, user selection of an option to terminate a telestration element, user selection of an option to remove a telestration element from a display, and/or any other suitable telestration termination event. Various telestration termination events may also be automatically detected, for example, an expiration of a predetermined time interval associated with the telestration element, a particular shape of the telestration element, and/or any other suitable telestration termination event that may be automatically detected. Systems and methods described herein may further indicate (e.g., graphically or audibly), subsequent to the telestration termination event and within the second image, an option to again render the telestration element at the 3D position. Various graphical indicators may be used to indicate an option to again render the telestration element, including but not limited to, pins, arrows, symbols, menu options, and any other suitable graphical indicator.

Various audible indicators may also be used to indicate an option to again render the telestration element, including but not limited to, voice commands and any other suitable audible indicator.

In some examples, system 100 may determine a telestration mode based on user input selecting a particular type of telestration that is desired. Additionally or alternatively, system 100 may automatically determine a telestration mode based on a context within which a telestration element is provided and/or any other suitable factor. As used herein, a telestration mode may include, without limitation, a free-form mode, an object selection mode, and a fiducial marker mode.

In the free-form mode, the telestration element to be drawn within an image depicting a scene may include, without limitation, any suitable drawing or graphical item that is to be rendered within a corresponding 3D image of the scene. For example, the telestration element may include a geometric shape, a word, a symbol, a mark, or any suitable drawing or graphical item. The telestration element may also be used for various forms of communication, for example, between surgical team members, between a surgical team member and the telestration element management system, and/or between a surgical team member and another component of a surgical system (e.g., a shape of the telestration element may be interpreted by optical character recognition and provided as a command to system 100 and/or a surgical system component).

In the object selection mode, the telestration element may be used to select an object within the image. For example, while in the object selection mode, a user may draw a circle around an or otherwise provide an indication of a selection of an object portrayed in the image. As described herein, the object selection may be graphically rendered within the 3D image.

In the fiducial marker mode, the telestration element may be used to place, on the image, fiducial markers that may be graphically rendered within the 3D image. Examples of this are provided herein.

The user may provide user input to system 100 that includes, without limitation, drawing a telestration element on the image, selecting a telestration mode, and/or any other suitable user input. Such user input may be provided in any suitable manner. For example, user input drawing a telestration element on the image or placing a graphic item as a telestration element on the image may include, without limitation, the user drawing on a touchscreen, the user drawing on the image using an input device, the user selecting and placing a graphic item on the image, and/or the user providing a telestration element in any other suitable manner. In another example, user input selecting a telestration mode may include, without limitation, the user selecting an option displayed in an image, the user selecting a user input button on a component of a computer-assisted surgical system, the user providing a verbal command, and/or the user selecting a telestration mode in any other suitable manner.

Telestration modes and rendering of telestration elements with spatial memory, temporal memory, and/or user memory, will now be described in more detail.

Figure 6:
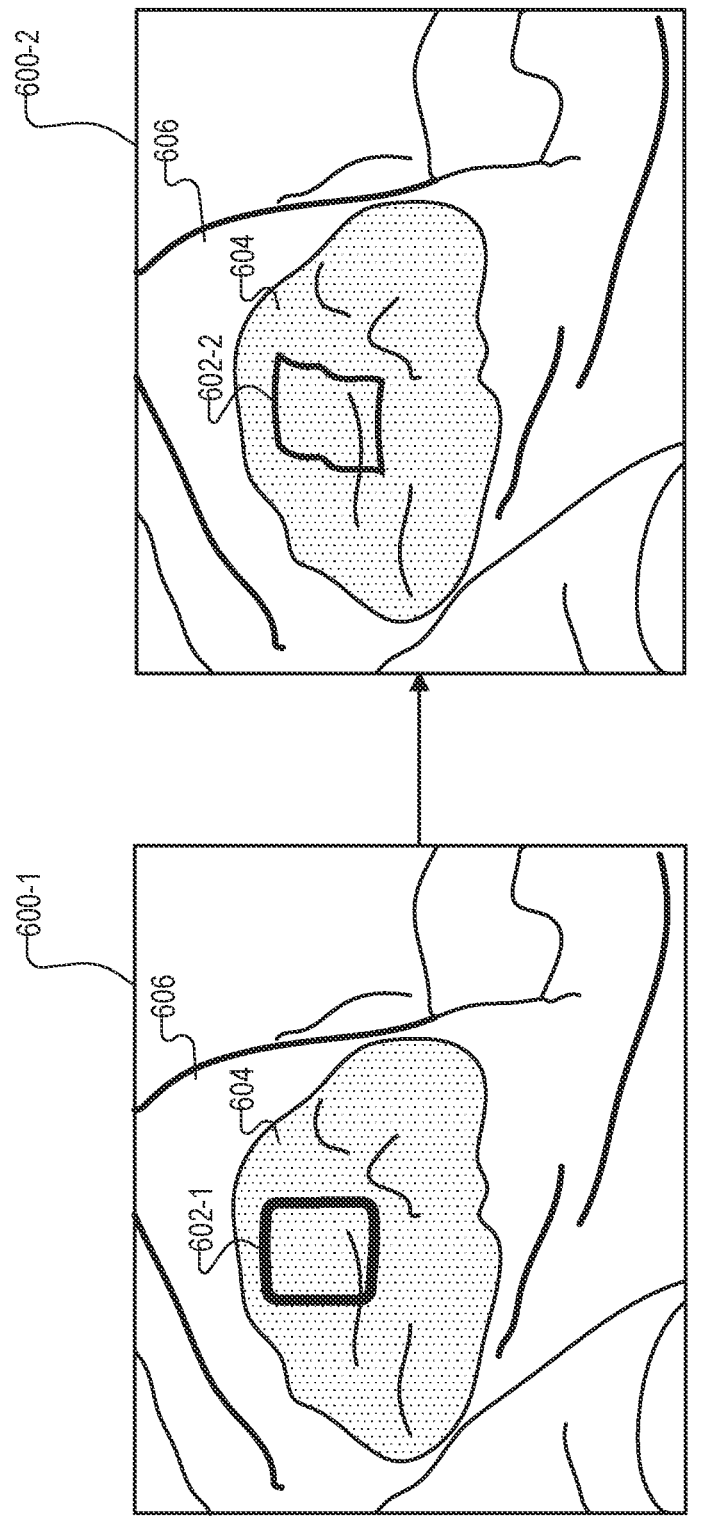
FIGS. 6-8 illustrate exemplary telestration elements drawn on a 2D image and rendered within a 3D image according to principles described herein.

FIG. 6 shows an example of a free form mode of telestration. FIG. 6 shows an exemplary 2D image 600-1 that may be captured by an imaging device aimed at an internal space of a patient and that may be represented by image data 202. FIG. 6 further shows an exemplary 3D image 600-2 that correlates to image 600-1 and that may be represented by image data 202 and depth data 204. As shown, in a free-form mode, a telestration element 602-1 is drawn by a user as user input on image 600-1, which for example depicts a tissue defect 604 surrounded by non-defective tissue 606. Although telestration element 602-1 is drawn as a rectangle over a particular area of tissue defect 604, telestration element 602-1 may be any suitable shape or size and may be drawn on any suitable part of the scene in 2D image 600-1.

In a free-form mode, system 100 may detect that a user inputs a telestration element on a 2D image depicting a surface within a scene and renders, based on image data 202, depth data 204, and the user input, a correlating telestration element 602-2 at a 3D position within a corresponding 3D image depicting the surface within the scene. For example, system 100 may identify, based on the user input drawing of telestration element 602-1, a plurality of pixels within the 2D image 600-1 represented by image data 202 that correlate to the telestration element 602-1. System 100 may determine, based on depth data 204, depth values for each of the plurality of pixels that correlate to the telestration element 602-1 to identify 3D position data for rendering the telestration element at a 3D position within 3D image 600-2. The telestration element 602-2 that correlates to telestration element 602-1 is then shown to be rendered over an identified 3D position within 3D image 600-2 (e.g., to visually appear as being in physical contact with the surface within the scene).

While telestration element 602-2 is illustrated as being a contoured rectangle positioned over a portion of tissue defect 604, it will be recognized that telestration element 602-2 may alternatively be rendered in any other suitable manner. For example, telestration element 602-2 may be at least partially transparent or rendered with partial lines to allow visualization by the user of the 3D image 600-2 and/or tissue defect 604 while telestration element 602-2 is rendered over the 3D position.

In some examples, the 2D image 600-1 on which telestration element 602-1 is provided may be displayed by a first display system (e.g., a single display device accessible by surgical team members) and the 3D image 600-2 within which telestration element 602-2 is rendered may be displayed by a second display system (e.g., display devices included in a stereo viewer used by a surgeon). In some examples, the first display system may be located in a different room than the second display system.

Figure 7:
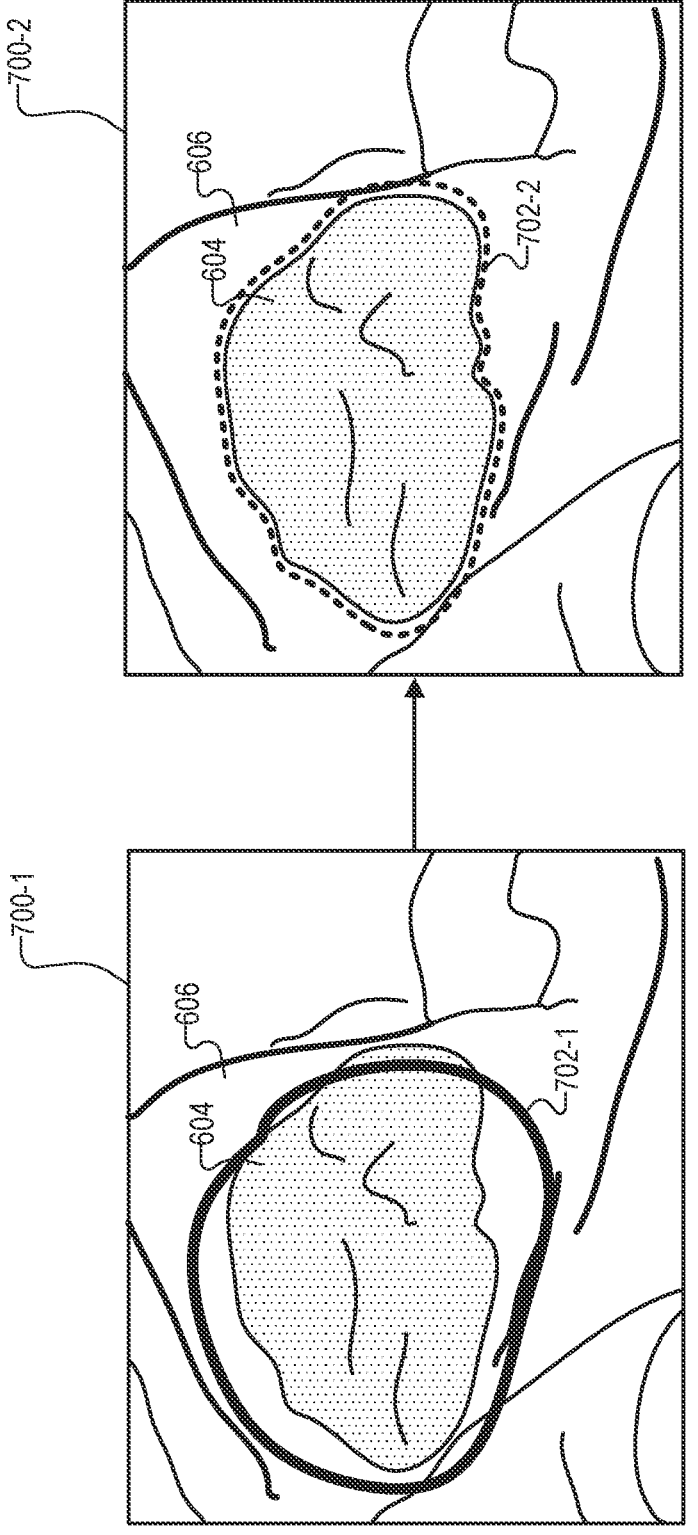

FIG. 7 shows an exemplary object selection mode of telestration. In particular, FIG. 7 shows an exemplary 2D image 700-1 that may be captured by an imaging device aimed at an internal space of a patient and that may be represented by image data 202. FIG. 7 further shows an exemplary 3D image 700-2 that correlates to image 700-1 and that may be represented by image data 202 and depth data 204. As shown, in an object selection mode, a telestration element 702-1 is drawn by a user as user input on 2D image 700-1, which for example depicts a tissue defect 604 surrounded by non-defective tissue 606. As shown, the telestration element 702-1 may be drawn as a circular shape around most but not all of tissue defect 604. In object selection mode, this drawing is indicative of an attempt by the user to select the tissue defect 604. Telestration element 702-1 may be drawn in any other suitable shape or manner as may serve a particular implementation.

System 100 may detect the selection of an object in any suitable way. For example, although telestration element 702-1 is not completely surrounding tissue defect 604, system 100 is able to detect the selection of tissue defect 604 by applying a classification heuristic to image data 202, depth data 204, and a user input of 2D pixel coordinates representative of pixels correlated to a drawing of the telestration element on the 2D image. A telestration element 702-2 that surrounds (and may show selection of) tissue defect 604 is then shown to be rendered over an identified 3D position within the 3D image 700-2. As shown, telestration element 702-2 follows the actual outline of tissue defect 604 instead of looking like telestration element 702-1. In this manner, as described in more detail below, visual artifacts that may result from telestration element 702-1 being rendered on different surfaces within 3D image 700-2 may be reduced or prevented.

Although telestration element 702-2 is shown by dashed lines around tissue defect 604, any other suitable graphic indication may be used to show object selection, including but not limited to, highlighting the object, shading the object with color, outlining the object with a different line, and/or any other suitable graphic indication. Although telestration element 702-2 is shown to surround a tissue defect, any internal anatomy of the patient (e.g., vessels, organs, and/or tissue), any surgical instrument, and/or any other suitable object located in the internal space may be selected in the object selection mode as well.

In an object selection mode, system 100 may detect that a user selects an object in the 2D image and identify the 3D position of the object within the 3D image based on image data 202, depth data 204, and user input of 2D pixel coordinates, in any suitable manner. For example, system 100 may detect a selection of an object by applying image data 202, depth data 204, and the user input of 2D pixel coordinates, to a classification heuristic and performing the classification heuristic to identify and select the object within the 3D image.

For example, based on image data 202, depth data 204, and user input of 2D pixel coordinates, system 100 may segment the 3D image (e.g., by classifying different portions of the image as corresponding to different items (e.g., types of tissue, organs, or objects). Based on the segmentation, system 100 may determine one or more characteristics of the surgical area and/or the surface onto which the telestration element is to be rendered, such as identifying the object, identifying the 3D position of the object, determining tissue type, etc.

In another example, system 100 may identify the object by inputting the image data 202, depth data 204, and the user input of 2D pixel coordinates into a machine learning model configured to identify objects. The machine learning model may be trained and/or used in any suitable manner.

Advantageously, the object selection mode of telestration renders the telestration element neatly in the 3D image without visual artifacts that could occur if the 3D rendering is dropped to a surface below than otherwise intended by the telestration element drawn by the user on the 2D image. For example, a user may attempt to select an end of a tool that is in the scene by drawing a circle around the end of the tool on the 2D image. Here, it may not be desirable to render the telestration element down to the entire surface underneath the drawn telestration element on the 2D image if the circle has not been exactly drawn around the end of the tool since some portions of the telestration element may be rendered within the 3D image as being on the tool and other portions may be rendered as being on a tissue surface behind the tool. Hence, a classification heuristic (e.g., machine learning, segmentation, etc.) may be used to determine that the user really intended to select the end of the tool. In response, system 100 may redraw or otherwise adjust the 2D drawing to be on the perimeter of the end of the tool so that when it is rendered within the 3D image, the telestration element is only on the tool and not on unintended surfaces beneath the telestration element drawn by the user on the 2D image.

Figure 8:
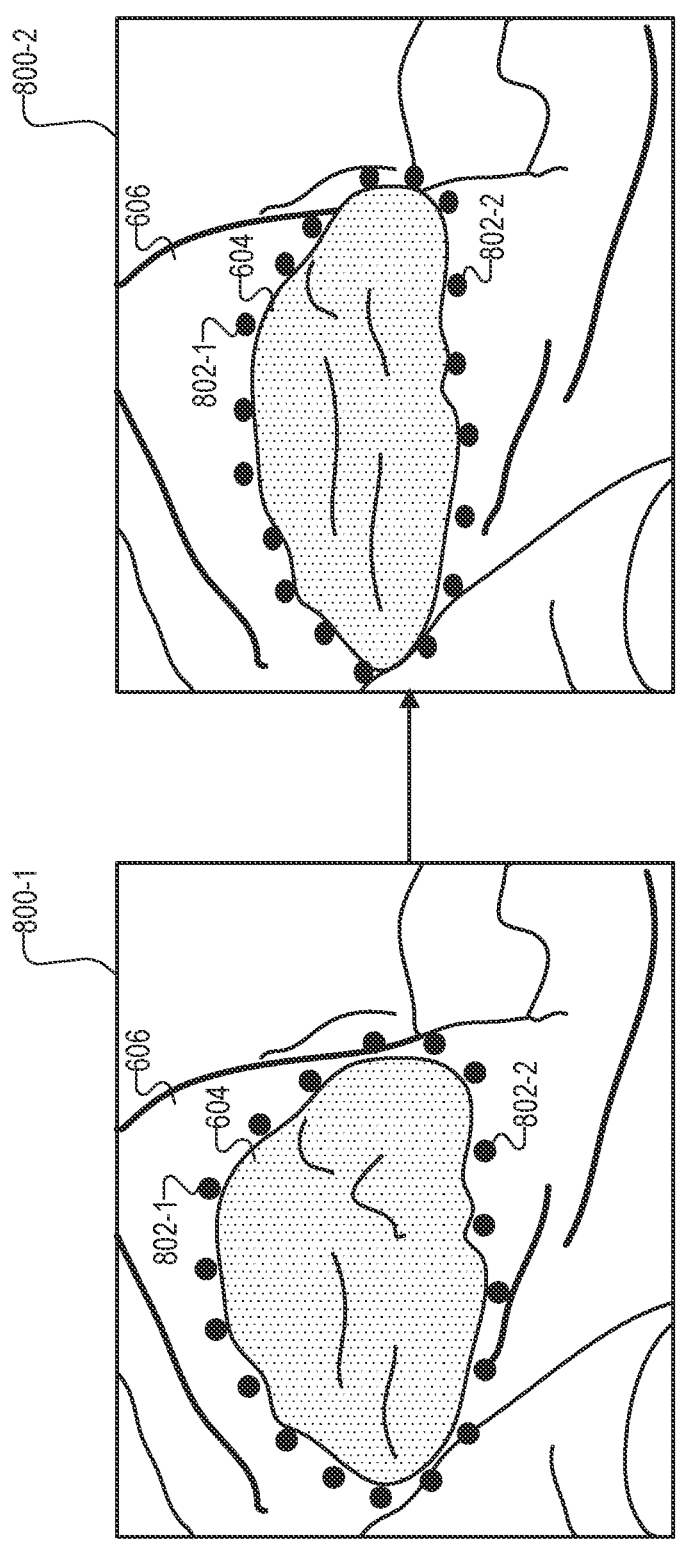

In FIG. 8, an example is shown of a fiducial marker mode of telestration. FIG. 8 shows an exemplary 2D image 800-1 that may be captured by an imaging device aimed at an internal space of a patient and that may be represented by image data 202. FIG. 8 further shows an exemplary 3D image 800-2 that correlates to 2D image 800-1 and that may be represented by image data 202 and depth data 204. As shown, in a fiducial marker mode, a user may draw a plurality of fiducial markers 802 (e.g., fiducial markers 802-1 and 802-2) on image 800-1, which for example depicts a tissue defect 604 surrounded by non-defective tissue 606. Fiducial markers 802 constitute a plurality of telestration events and may be used for various purposes such as guiding an excision, suturing process, and/or any other procedure.

As shown, fiducial markers 802 may be rendered within 3D image 800-2. In some examples, system 100 may recognize that the telestration events are fiducial markers 802 and, in response, cause fiducial markers 802 to remain in place with the anatomy of tissue defect 604 even if tissue is moved or stretched. For example, the tissue shown in 3D image 800-2 is stretched compared to the tissue shown in 2D image 800-1. However, the fiducial markers 802 have moved to stay in their relative positions with respect to tissue defect 604.

Figure 9:
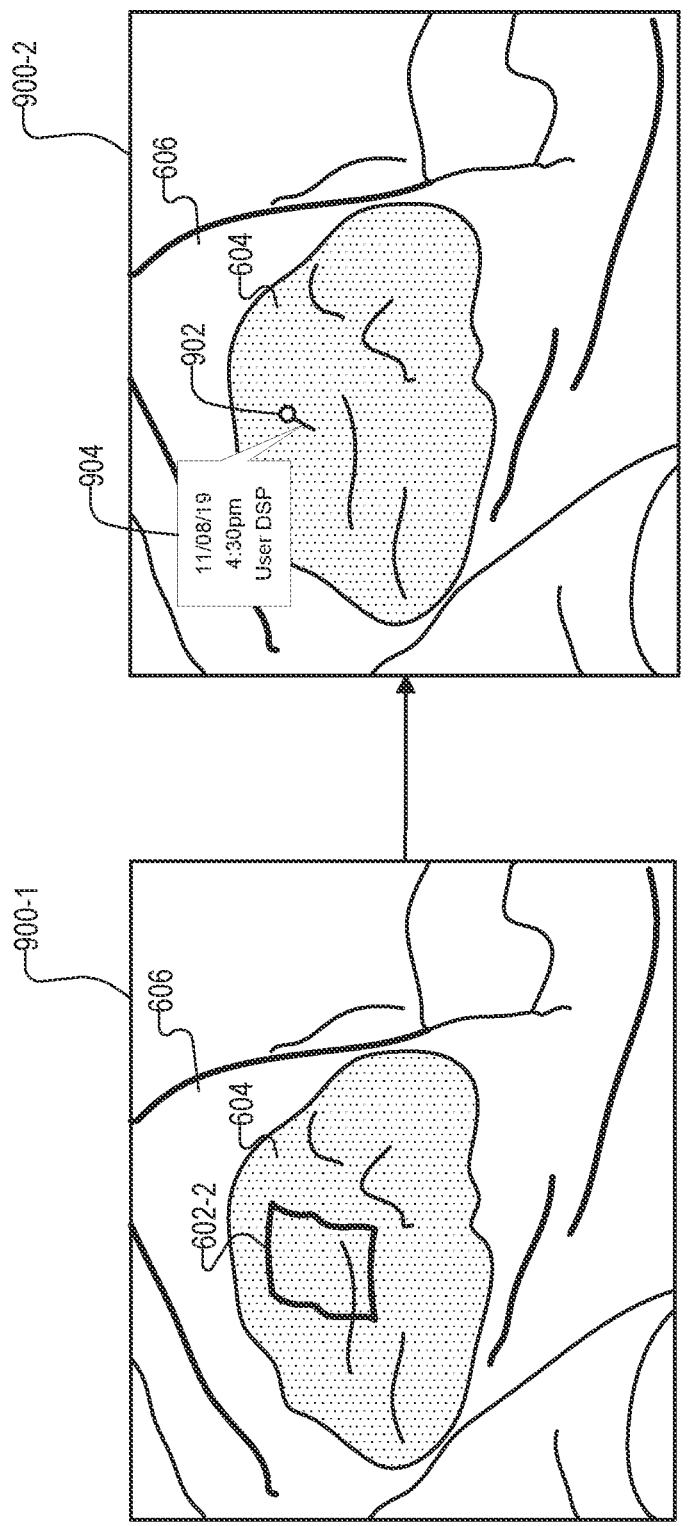
FIG. 9 illustrates an exemplary selectable graphical indicator and an exemplary timestamp associated with a telestration element within an image according to principles described herein.

FIG. 9 shows an exemplary selectable graphical indicator 902 and an exemplary timestamp 904 placed at a position within 3D image 900-2 where telestration element 602-2 was previously rendered, as shown in FIG. 6. FIG. 9 shows an exemplary 3D image 900-1 that may be captured by an imaging device aimed at an internal space of a patient and that may be represented by image data 202 and depth data 204. After a telestration termination event is detected, telestration element 602-2 is removed from 3D image 900-1 and replaced by selectable graphical indicator 902, which is illustrated as a pin within 3D image 900-2 at a center position of previously rendered telestration element 602-2. In certain examples, selectable graphical indicator 902 may be permanently recorded at the 3D position of a rendered telestration element and viewed by a user at any time during the surgical procedure. When a first user input representative of a selection of graphical indicator 902 (e.g., a user hovers a cursor over the pin) is received, system 100 may display a timestamp 904 including date and time information. Optionally, user information may also be included in timestamp 904. When another user input representative of a selection of graphical indicator 902 (e.g., a user clicks on the pin) is received, system 100 may again render telestration element 602-2 within 3D image 900-2 in response to the user input.

Figure 10:
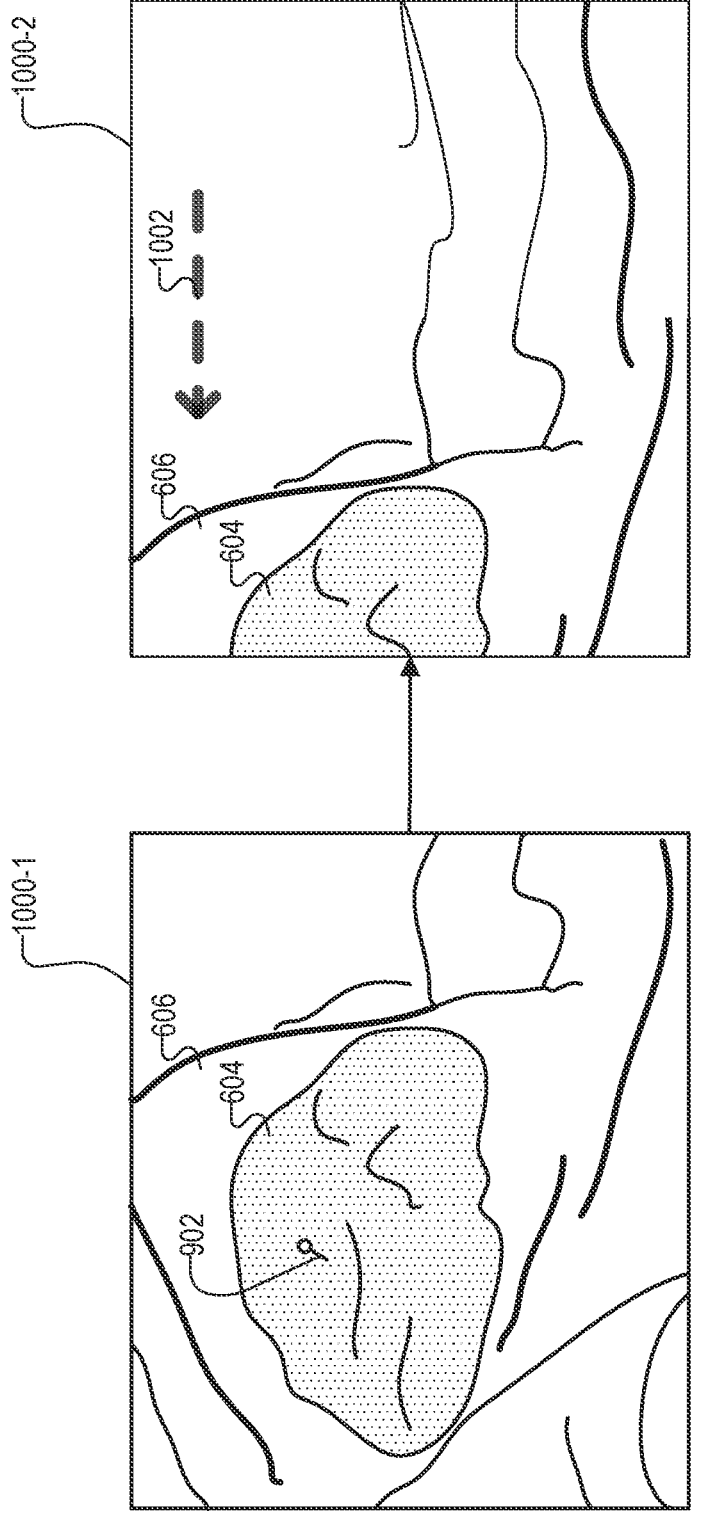
FIG. 10 illustrates an exemplary directional graphical indicator that points to a position of a telestration element according to principles described herein.

FIG. 10 illustrates an exemplary directional graphical indicator 1002 that points to a position (e.g., a 3D position) of a telestration element. FIG. 10 shows an exemplary 3D image 1000-1 that may be captured by an imaging device aimed at an internal space of a patient and that may be represented by image data 202 and depth data 204. As shown previously, graphical indicator 902 replaced a previously rendered telestration element 602-2 after a telestration termination event. 3D image 1000-2 illustrates a changed scene, for example when a camera is moved, that removes graphical indicator 902 from view. In such a case, system 100 may display directional graphical indicator 1002, such as an arrow, that points in the direction of graphical indicator 902 to advantageously alert the user or surgeon to a location of a previously rendered telestration element presently out of view, such as telestration element 602-2. The user may then navigate to the area of the rendered telestration element and see a selectable graphical indicator (e.g. selectable graphical indicator 902) which may be optionally selected. Various directional graphical indicators may be used to indicate the location of a previously rendered telestration element, including, without limitation, arrows, symbols, menu options, and any other suitable directional graphical indicator.

Figure 11:
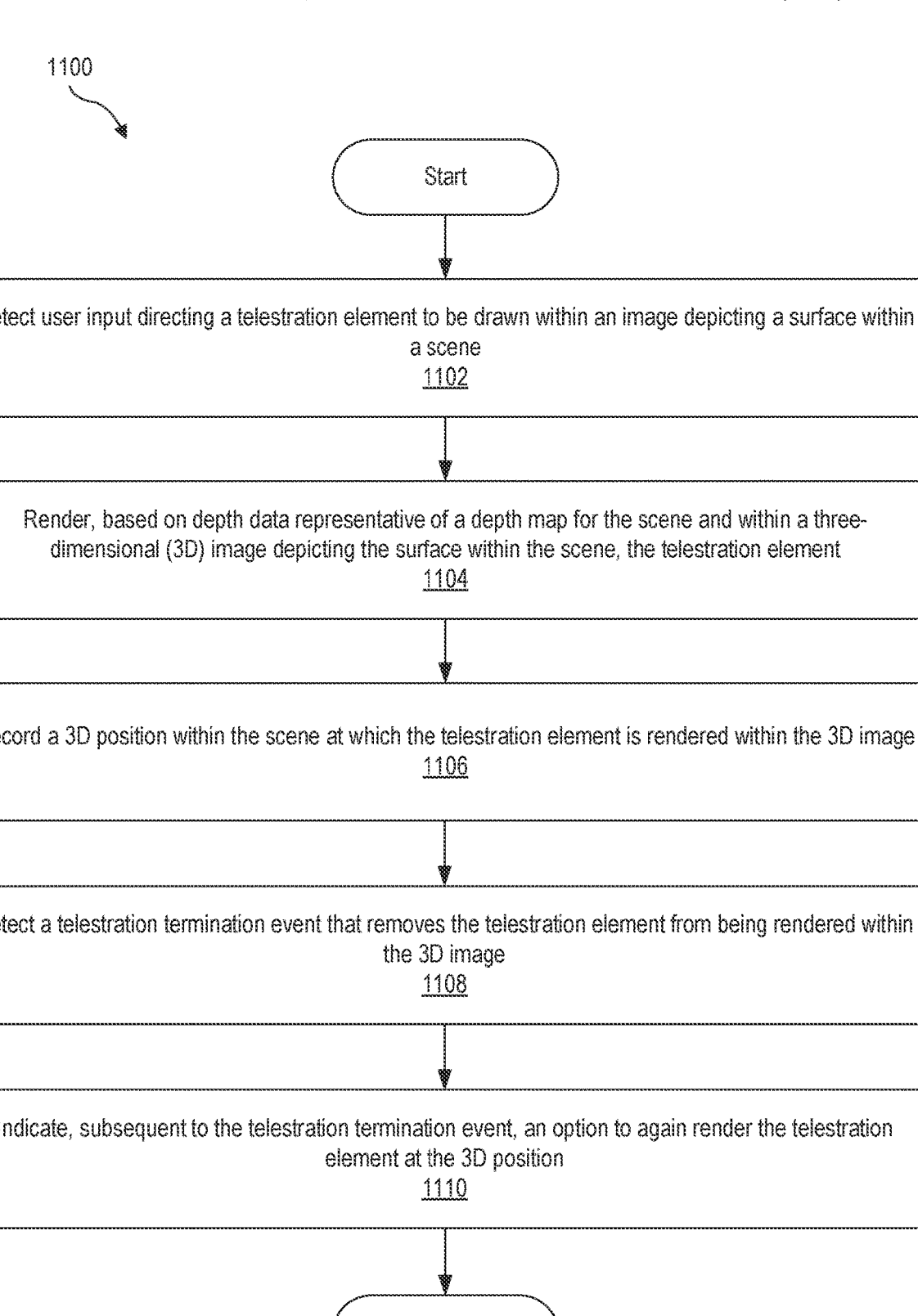
FIG. 11 illustrates an exemplary method according to principles described herein.

FIG. 11 illustrates an exemplary method 1100 that may be performed by a telestration element management system (e.g., system 100 and/or any implementation thereof). While FIG. 11 illustrates exemplary operations according to one embodiment, other embodiments may omit, add to, reorder, and/or modify any of the operations shown in FIG. 11.

In operation 1102, a telestration element management system detects user input directing a telestration element to be drawn within an image depicting a surface within a scene. Operation 1102 may be performed in any of the ways described herein.

In operation 1104, the telestration element management system renders, based on depth data representative of a depth map for the scene and within a three-dimensional (3D) image depicting the surface within the scene, the telestration element. Operation 1104 may be performed in any of the ways described herein.

In operation 1106, the telestration element management system records a 3D position within the scene at which the telestration element is rendered within the 3D image. Operation 1106 may be performed in any of the ways described herein.

In operation 1108, the telestration element management system detects a telestration termination event that removes the telestration element from being rendered within the 3D image. Operation 1108 may be performed in any of the ways described herein.

In operation 1110, the telestration element management system indicates, subsequent to the telestration termination event, an option to again render the telestration element at the 3D position. Operation 1110 may be performed in any of the ways described herein.

Figure 12:
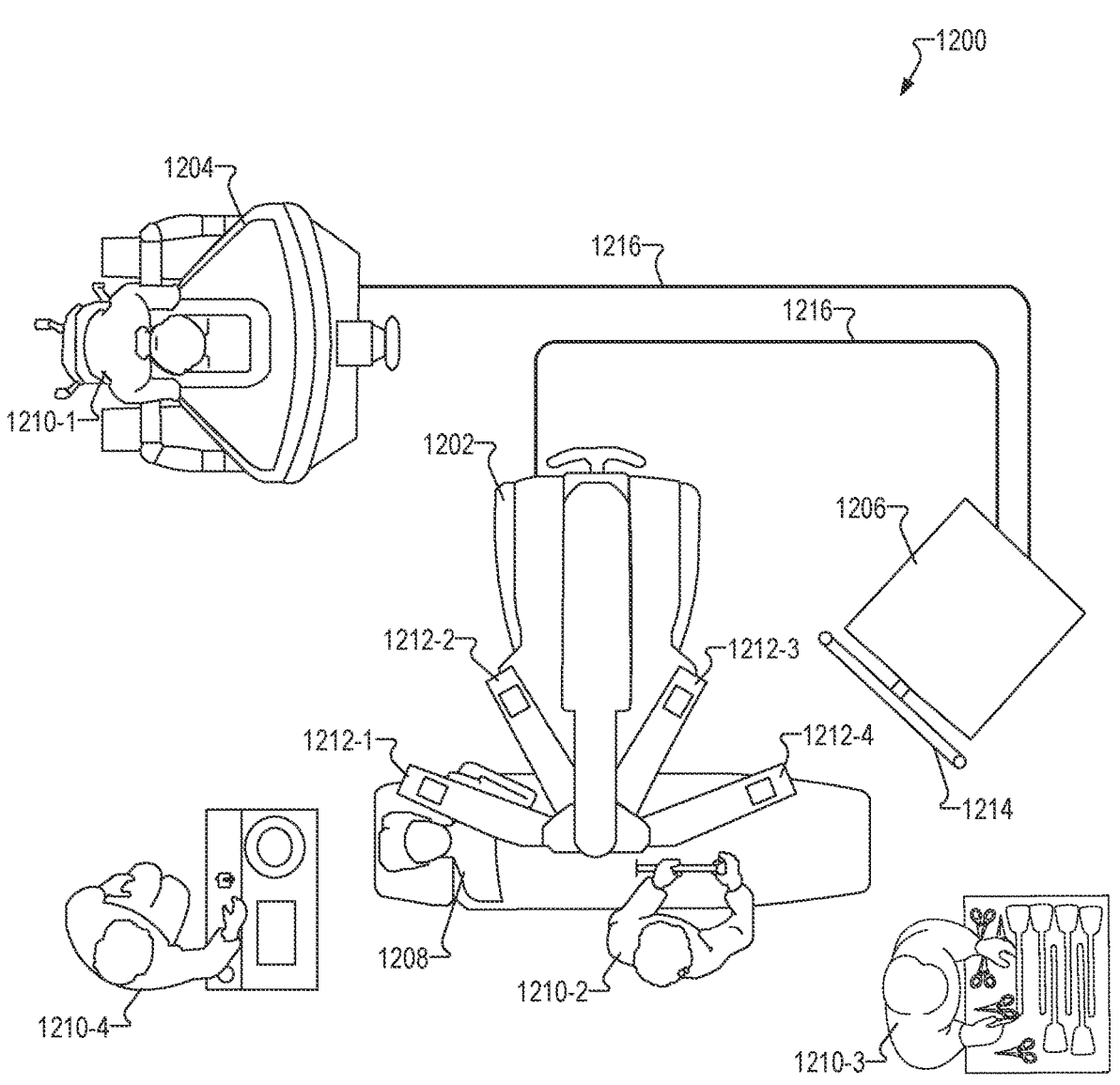
FIG. 12 illustrates an exemplary computer-assisted surgical system according to principles described herein.

The systems and methods described herein may be used in connection with and/or implemented by a computer-assisted surgical system used to perform a surgical procedure with respect to a patient. FIG. 12 illustrates an exemplary computer-assisted surgical system 1200 ("surgical system 1200"). As shown, surgical system 1200 may include a manipulating system 1202, a user control system 1204, and an auxiliary system 1206 communicatively coupled one to another. Surgical system 1200 may be utilized by a surgical team to perform a computer-assisted surgical procedure on a patient 1208. As shown, the surgical team may include a surgeon 1210-1, an assistant 1210-2, a nurse 1210-3, and an anesthesiologist 1210-4, all of whom may be collectively referred to as "surgical team members 1210." Additional or alternative surgical team members may be present during a surgical session as may serve a particular implementation.

While FIG. 12 illustrates an ongoing minimally invasive surgical procedure, it will be understood that surgical system 1200 may similarly be used to perform open surgical procedures or other types of surgical procedures that may similarly benefit from the accuracy and convenience of surgical system 1200. Additionally, it will be understood that the surgical session throughout which surgical system 1200 may be employed may not only include an operative phase of a surgical procedure, as is illustrated in FIG. 12, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 12, manipulating system 1202 may include a plurality of manipulator arms 1212 (e.g., manipulator arms 1212-1 through 1212-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 1208 (e.g., by being at least partially inserted into patient 1208 and manipulated to perform a computer-assisted surgical procedure on patient 1208). Mile manipulating system 1202 is depicted and described herein as including four manipulator arms 1212, it will be recognized that manipulating system 1202 may include only a single manipulator arm 1212 or any other number of manipulator arms as may serve a particular implementation.

Manipulator arms 1212 and/or surgical instruments attached to manipulator arms 1212 may include one or more displacement transducers, orientational sensors, and/or positional sensors used to generate raw (i.e., uncorrected) kinematics information. One or more components of surgical system 1200 may be configured to use the kinematics information to track (e.g., determine positions of) and/or control the surgical instruments.

User control system 1204 may be configured to facilitate control by surgeon 1210-1 of manipulator arms 1212 and surgical instruments attached to manipulator arms 1212. For example, surgeon 1210-1 may interact with user control system 1204 to remotely move or manipulate manipulator arms 1212 and the surgical instruments, To this end, user control system 1204 may provide surgeon 1210-1 with imagery (e.g., high-definition 3D imagery) of a surgical area associated with patient 1208 as captured by an imaging system (e.g., any of the medical imaging systems described herein). In certain examples, user control system 1204 may include a stereo viewer having two displays where stereoscopic images of a surgical area associated with patient 1208 and generated by a stereoscopic imaging system may be viewed by surgeon 1210-1. Surgeon 1210-1 may utilize the imagery to perform one or more procedures with one or more surgical instruments attached to manipulator arms 1212.

To facilitate control of surgical instruments, user control system 1204 may include a set of master controls. These master controls may be manipulated by surgeon 1210-1 to control movement of surgical instruments (e.g., by utilizing robotic and/or teleoperation technology). The master controls may be configured to detect a wide variety of hand, wrist, and finger movements by surgeon 1210-1. In this manner, surgeon 1210-1 may intuitively perform a procedure using one or more surgical instruments.

Auxiliary system 1206 may include one or more computing devices configured to perform primary processing operations of surgical system 1200. In such configurations, the one or more computing devices included in auxiliary system 1206 may control and/or coordinate operations performed by various other components (e.g., manipulating system 1202 and user control system 1204) of surgical system 1200. For example, a computing device included in user control system 1204 may transmit instructions to manipulating system 1202 by way of the one or more computing devices included in auxiliary system 1206. As another example, auxiliary system 1206 may receive, from manipulating system 1202, and process image data representative of imagery captured by an imaging device attached to one of manipulator arms 1212.

In some examples, auxiliary system 1206 may be configured to present visual content to surgical team members 1210 who may not have access to the images provided to surgeon 1210-1 at user control system 1204. To this end, auxiliary system 1206 may include a display monitor 1214 configured to display one or more user interfaces, such as images (e.g., 2D images, 3D images) of the surgical area, information associated with patient 1208 and/or the surgical procedure, and/or any other visual content as may serve a particular implementation. For example, display monitor 1214 may display images of the surgical area together with additional content (e.g., graphical content, contextual information, etc.) concurrently displayed with the images. In some embodiments, display monitor 1214 is implemented by a touchscreen display with which surgical team members 1210 may interact (e.g., by way of touch gestures) to provide user input to surgical system 1200.

Manipulating system 1202, user control system 1204, and auxiliary system 1206 may be communicatively coupled one to another in any suitable manner. For example, as shown in FIG. 12, manipulating system 1202, user control system 1204. and auxiliary system 1206 may be communicatively coupled by way of control lines 1216, which may represent any wired or wireless communication link as may serve a particular implementation. To this end, manipulating system 1202, user control system 1204, and auxiliary system 1206 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 13:
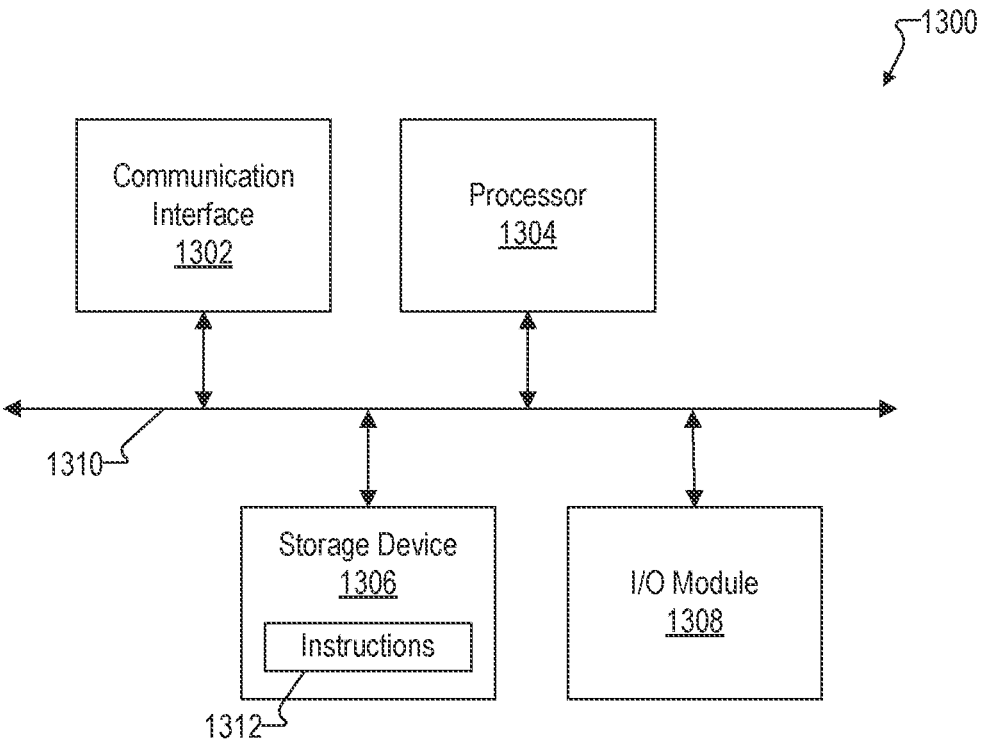
FIG. 13 illustrates an exemplary computing device according to principles described herein.

FIG. 13 illustrates an exemplary computing device 1300 that may be specifically configured to perform one or more of the processes described herein. Any of the systems, computing devices, and/or other components described herein may be implemented by computing device 1300.

As shown in FIG. 13, computing device 1300 may include a communication interface 1302, a processor 1304, a storage device 1306, and an input/output ("I/O") module 1308 communicatively connected one to another via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data and/or interpreting, executing, and/or directing execution of one or more of the instructions, processes, and/or operations described herein. Processor 1304 may perform operations by executing computer-executable instructions 1312 (e.g., an application, software, code, and/or other executable data instance) stored in storage device 1306.

Storage device 1306 may include one or more data storage media, devices, or configurations and may employ any type, form, and combination of data storage media and/or device. For example, storage device 1306 may include, but is not limited to, any combination of the non-volatile media and/or volatile media described herein. Electronic data, including data described herein, may be temporarily and/or permanently stored in storage device 1306. For example, data representative of computer-executable instructions 1312 configured to direct processor 1304 to perform any of the operations described herein may be stored within storage device 1306. In some examples, data may be arranged in one or more databases residing within storage device 1306.

I/O module 1308 may include one or more I/O modules configured to receive user input and provide user output. I/O module 1308 may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions; and
a processor communicatively coupled to the memory and configured to execute the instructions to:
detect user input directing a telestration element to be drawn within an image depicting a surface within a scene;
render, based on depth data representative of a depth map for the scene and within a three-dimensional (3D) image depicting the surface within the scene, the telestration element, the 3D image acquired by an imaging device while the imaging device is aimed at an internal space of a patient;
record a 3D position within the scene at which the telestration element is rendered within the 3D image;
detect a telestration termination event that removes the telestration element from being rendered within the 3D image;
indicate, subsequent to the telestration termination event, an option to again render the telestration element at the 3D position, the indicating comprising presenting, while the telestration element is removed from being rendered within the 3D image, a selectable graphical indicator at a position within the 3D image where the telestration element was rendered, wherein a selection of the selectable graphical indicator causes the processor to again render the telestration element at the 3D position; and
display, within an additional 3D image acquired by the imaging device while the imaging device is aimed at a different internal space of the patient and that does not depict the position within the 3D image where the telestration element was rendered, a directional graphical indicator that points in a direction of the position within the 3D image where the telestration element was rendered.

2. The system of claim 1, wherein the detecting of user input comprises detecting that the user selects, in the image, an object including the surface within the scene.

3. The system of claim 2, wherein the processor is further configured to execute the instructions to perform a classification heuristic with respect to the scene, and wherein the detecting that the user selects the object is based on the performing of the classification heuristic.

4. The system of claim 1, wherein the detecting of user input comprises detecting that the user places fiducial markers on the image depicting the surface within the scene.

5. The system of claim 1, wherein the processor is further configured to execute the instructions to:
access image data representative of the 3D image acquired by the imaging device;
obtain the depth data;
identify, based on the image data and the depth data, a plurality of pixels within the 3D image that depicts the 3D position at which the telestration element is to be rendered; and
designate the plurality of pixels as the 3D position.

6. The system of claim 5, wherein the imaging device comprises a visible light camera and the image acquired by the imaging device comprises a two-dimensional visible light image acquired by the visible light camera.

7. The system of claim 6, wherein the obtaining of the depth data comprises directing a depth sensor in the imaging device and separate from the visible light camera to acquire the depth data while the imaging device is aimed at the internal space of the patient.

8. The system of claim 7, wherein the depth sensor comprises a time-of-flight sensor.

9. The system of claim 5, wherein the obtaining of the depth data comprises:

directing a first visible light camera included in the imaging device to acquire a first visible light image of the internal space;

directing a second visible light camera included in the imaging device to acquire a second visible light image of the internal space; and generating, based on the first and second visible light images, the depth data.

10. The system of claim 1, wherein the rendering of the telestration element is at least partially transparent to allow visualization by a user while the telestration element is rendered at the 3D position.

11. The system of claim 1, wherein the processor is further configured to execute the instructions to:

receive user input representative of the selection of the graphical indicator; and again render the telestration element at the 3D position in response to the user input.

12. The system of claim 1, wherein the processor is further configured to execute the instructions to:

determine a timestamp representative of when the telestration element is first rendered; and present, subsequent to the telestration termination event, the timestamp.

13. The system of claim 1, wherein the image is displayed by a first display system and the 3D image is displayed by a second display system.

14. The system of claim 13, wherein the first display system is located in a different room than the second display system.

15. The system of claim 1, wherein the image depicting the surface within the scene is a two-dimensional (2D) image.

16. The system of claim 15, wherein the telestration termination event removes the telestration element from being drawn on the 2D image.

17. The system of claim 1, wherein the rendering of the telestration element comprises rendering the telestration element to visually appear as being in physical contact with the surface depicted by the 3D image.

18. A system comprising:

a memory storing instructions; and a processor communicatively coupled to the memory and configured to execute the instructions to:

detect user input directing a telestration element to be drawn within a first image depicting a scene;

render, in response to the user input, the telestration element within a second image depicting the scene, the second image acquired by an imaging device while the imaging device is aimed at an internal space of a patient;

record a position within the scene at which the telestration element is rendered within the second image;

detect a telestration termination event that removes the telestration element from being rendered within the second image;

indicate, subsequent to the telestration termination event and within the second image, an option to again render the telestration element within the second image at the position, the indicating comprising presenting, while the telestration element is removed from being rendered within the second image, a selectable graphical indicator at a position within the second image where the telestration element was rendered, wherein a selection of the selectable graphical indicator causes the processor to again render the telestration element at the position; and display, within an additional image acquired by the imaging device while the imaging device is aimed at a different internal space of the patient and that does not depict the position within the second image where the telestration element was rendered, a directional graphical indicator that points in a direction of the position within the second image where the telestration element was rendered.

19. A method comprising:

detecting, by a telestration element management system, user input directing a telestration element to be drawn within an image depicting a surface within a scene;

rendering, by the telestration element management system based on depth data representative of a depth map for the scene and within a three-dimensional (3D) image depicting the surface within the scene, the telestration element, the 3D image acquired by an imaging device while the imaging device is aimed at an internal space of a patient;

recording, by the telestration element management system, a 3D position within the scene at which the telestration element is rendered within the 3D image;

detecting, by the telestration element management system, a telestration termination event that removes the telestration element from being rendered within the 3D image; and indicating, by the telestration element management system subsequent to the telestration termination event, an option to again render the telestration element at the 3D position, the indicating comprising presenting, while the telestration element is removed from being rendered within the 3D image, a selectable graphical indicator at a position within the 3D image where the telestration element was rendered, wherein a selection of the selectable graphical indicator causes the telestration element management system to again render the telestration element at the 3D position; and displaying, by the telestration element management system within an additional 3D image acquired by the imaging device while the imaging device is aimed at a different internal space of the patient and that does not depict the position within the 3D image where the telestration event was rendered, a directional graphical indicator that points in a direction of the position within the 3D image where the telestration event was rendered.

20. The method of claim 19, further comprising:

accessing, by the telestration element management system, image data representative of the 3D image acquired by the imaging device;

obtaining, by the telestration element management system, the depth data;

identifying, by the telestration element management system based on the image data and the depth data, a plurality of pixels within the 3D image that depicts the 3D position at which the telestration element is to be rendered; and designating, by the telestration element management system, the plurality of pixels as the 3D position.

* * * * *